US006242564B1

(12) United States Patent
Pert et al.

(10) Patent No.: US 6,242,564 B1
(45) Date of Patent: Jun. 5, 2001

(54) TREATMENT OF TROPICAL SPASTIC PARESIS WITH PEPTIDE T

(76) Inventors: Candace B. Pert; Michael R. Ruff, both of 10319 Glen Rd., Potomac, MD (US) 20854

( * ) Notice: Subject to any disclaimer, the term of this patent is extended or adjusted under 35 U.S.C. 154(b) by 0 days.

(21) Appl. No.: 07/898,691

(22) Filed: Jun. 15, 1992

Related U.S. Application Data

(63) Continuation-in-part of application No. 07/718,587, filed on Jun. 20, 1991, now abandoned, which is a continuation-in-part of application No. 07/568,616, filed on Aug. 16, 1990, which is a continuation of application No. 07/314,507, filed on Feb. 15, 1989, which is a continuation of application No. 07/048,148, filed on May 11, 1987, which is a continuation-in-part of application No. 06/878,586, filed on Jun. 26, 1986, now abandoned, which is a continuation-in-part of application No. 06/869,919, filed on Jun. 3, 1986.

(51) Int. Cl.[7] .................................................. A61K 37/02
(52) U.S. Cl. ........................................... 530/328; 530/328
(58) Field of Search .................................... 530/328, 329, 530/330; 514/15, 16, 17, 18

(56) References Cited

U.S. PATENT DOCUMENTS

| 4,689,398 | * | 8/1987 | Wu et al. | ............................... 530/327 |
| 5,063,206 | * | 11/1991 | Bridge et al. | ........................... 514/16 |

FOREIGN PATENT DOCUMENTS

| 0249390 | * | 12/1987 | (EP) . |
| 0249394 | * | 12/1987 | (EP) . |

OTHER PUBLICATIONS

Buzy et al., Am. J. Med. vol. 87(3) pp. 361–362 (Sep. 1989).*
Mayer et al., Int Conf AIDS vol. 6(3) p. 200 (Abstr. No. SB459) (1990).*
Bridge et al., Int Conf AIDS vol. 7(2) p. 79 (Abstr. No. THB90) (1991).*
Heseltine et al., Int Conf AIDS vol. 7(1) P. 183 (Abstr. No. MB2006) (1991).*

Rodgers–Johnson et al., Immunologic Mechanisms in Neurologic and Psychiatric Disease, Waksman (Ed.), Raven Press, New York, pp. 117–129 (1990).*
Rodgers–Johnson et al., Human Retrovirology: HTLV, Blattner (Ed.), Raven Press, New York, pp. 205–211 (1990).*
Corbin et al., 5th International Conference on Human Retrovirology, Kamamoto, Japan May 11–13, 1992 (Abstract).*
Rudinger, Peptide Hormones, Parsons (Ed.), U Park Press, Baltimore, pp. 1–7 (1976).*
Pert et al., Proc Natl Acad Sci USA, vol. 83, pp. 9254–9258 (1986).*

* cited by examiner

Primary Examiner—Anthony C. Caputa
Assistant Examiner—Karen A. Canella
(74) Attorney, Agent, or Firm—William J. Sapone; Coleman Sudol; Sapone P.C.

(57) ABSTRACT

Intranasal therapy using short peptides of the formula (I):

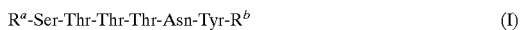

$$R^a\text{-Ser-Thr-Thr-Thr-Asn-Tyr-}R^b \quad \text{(I)}$$

where $R^a$ represents an amino terminal residue Ala-, D-Ala or Cys-Ala- and $R^b$ represents a carboxy terminal residue -Thr, -Thr-amide, -Thr-Cys or -Thr-Cys-amide, or a derivative thereof, or a peptide of formula (II):

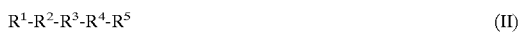

$$R^1\text{-}R^2\text{-}R^3\text{-}R^4\text{-}R^5 \quad \text{(II)}$$

where
$R^1$ is an amino terminal residue $XR^6$ or $R^6$ wherein $R^6$ is Thr-, Ser-, Asn-, Leu-, Ile-, Arg- or Glu- and X is Cys,
$R^2$ is Thr, Ser or Asp,
$R^3$ is Thr, Ser, Asn, Arg, Gln, Lys or Trp,
$R^4$ is Tyr and
$R^5$ is a carboxy terminal residue which is $R^7X$ or $R^7$ wherein $R^7$ may be any amino acid and X is Cys, or an ester or amide derivative thereof, or a physiologically acceptable salt of (I) or (II) is disclosed. Such peptides bind to T4 receptors and are useful for intranasal administration in preventing viral infectivity in mammals by viruses which bind to the T4 receptors. These peptides are believed to act as competitive blocking agents.

19 Claims, 4 Drawing Sheets

TREATMENT OF TROPICAL SPASTIC PARESIS WITH PEPTIDE T

This application is a continuation-in-part of Ser. No. 07/718,587 filed Jun. 20, 1991, now abandoned, which is a continuation-in-part of Ser. No. 07/568,616, filed Aug. 18, 1990, which is a continuation of Ser. No. 07/314,507 filed Feb. 15, 1989, which is a continuation of Ser. No. 07/048,148, filed May 11, 1987, which is a continuation-in-part of Ser. No. 06/878,586, filed Jun. 26, 1986, now abandoned which is a continuation-in-part of Ser. No. 06/869,919 filed Jun. 3, 1986.

BACKGROUND OF THE INVENTION

This invention relates to intranasal therapy using synthetically produced short peptide sequences which inhibit HTLV-III/LAV (hereinafter referred to as HIV) binding to human cells by blocking receptor sites on the cell surface, and thus preventing viral infectivity of human lymphocytes and other cells. The peptides, while preventing infectivity, also induce antibody production against the envelope protein of the HIV virus when appropriately coupled with carriers. Hence, these peptides also have use as vaccines to prevent development of Acquired Immune Deficiency Syndrome (AIDS). Monoclonal antibodies to the peptides could also be used as diagnostic agents to identify the HIV virus. Hence, peptides and antibodies to the peptides would have use in preparing test kits for identification of HIV carriers or persons suffering from AIDS.

The complete nucleotide sequence of the AIDS (HIV) virus has been reported by several investigators. (See Lee Ratner et al., *Nature* 313 p. 277, January 1985; Muesing et al., *Nature* 313 p. 450, February 1985; and Wain-Habson et al., *Cell* 40 pp. 9–17, January 1985) The envelope gene has been associated particularly with antigenicity and infectivity. However, the envelope portion is also known to have regions which are highly divergent. The HIV virus envelope glycoprotein has been shown to affix non-covalently to the brain membranes of humans, rats, and monkeys and to cells of the immune system.

The realization that viruses may exert cell and tissue tropism by attachment at highly specific sites on cell membrane receptors has encouraged investigators to seek agents which would bind at the viral receptor sites of cell membranes and thus prevent binding of a specific virus to these cells. A demonstration of specific receptor-mediated vaccinia virus infectivity being blocked by synthetic peptides has been previously demonstrated (Epstein et al., *Nature* 318: 663–667).

The HIV virus has been shown to bind to a surface molecule known as the CD4 or T4 region, which is present on various cells susceptible to HIV infection, including T lymphocytes and macrophages. (See Shaw et al., *Science* 226, pp. 1165–1171 for discussion of tropism of HTLV-III.)

In addition to symptoms arising from immunodeficiency, patients with AIDS show neuropsychological defects. The central nervous and immune systems share a large number of specific cell-surface recognition molecules, serving as receptors for neuropeptide-mediated intercellular communication. The neuropeptides and their receptors show profound evolutionary stability, being highly conserved in largely unaltered form in unicellular organisms as well as higher animals. Furthermore, the central nervous and immune systems show common, CD4 (T4) cell-surface recognition molecules which serve as receptors for the binding of HIV envelope glycoprotein (gp 120). Since the same highly conserved neuropeptide informational substances integrate immune and brain function through receptors remarkably similar to those of HIV, we postulated that a very similar amino acid sequence between the HIV glycoprotein gp 120 and a short peptide previously identified in another context from the envelope region of the Epstein Barr-Virus might indicate the core peptide essential for viral receptor binding. It was postulated that such a peptide would be useful in preventing infection of cells with the HIV by binding with receptor cells and blocking the binding of HIV gp 120, that such peptides binding to the receptor sites would give rise to production of antibodies directed to the peptide sequence, and that those peptides might be used to provide immunological basis for prevention of AIDS.

Recent basic research has demonstrated that common receptor and transmitter mechanisms may be found in the central nervous and cellular immune systems. Certain viruses may be able to utilize these common pathways to enter the cells in the brain as well as circulating leukocytes. Peptide T is a modified octapeptide homologous to a subunit sequence of Vasoactive Intestinal Peptide (VIP) described by Pert, et al (PNAS, Vol. 83, pages 9254–9258 (1986)) that was found to exist in homologous form in the 120 Kilodalton envelope glycoprotein (gp 120) of all HIV isolates thus far sequenced. Autoradiographic mapping with labeled gp 120 has shown greater binding in VIP receptor rich areas. In vitro studies have demonstrated that VIP and Peptide T inhibit both the binding of gp 120 to brain tissue and HIV replication in cell culture. Peptide T in picomolar concentrations has been shown to block the neurotoxic effects of gp 120 in cell culture and animals. Intravenous Peptide T in doses up to 224 mg/day has shown no toxicity and has resulted in improved neurocognitive functioning in the HIV-infected patients participating in a recent study. Rosen, M I, et al *Addiction* (Inpress)—Brenneman, D. et al (Nature 335 page 639–642, 1788; Bridge, T P et al, Lancet II page 226–227 (1989)—Hill, J. M. et al (abstract) Sixth Intl. conf. on AIDS vol. 1, page 330.

The clinical relevance of this observation has been recently underscored by the finding that HIV-1-induced neurotoxicity appears to be associated with gp 120-CD4 binding resulting in increasing intracellular free calcium. Calcium channel blockers such as nimodipine have been shown to antagonize this effect.

The present invention relates to the use of Peptide T in treating HIV-infected patients. These initial intravenous studies involved 20 AIDS and ARC patients who received the drug for one to three months without consistent changes in p24 antigen or immunologic measures but who manifested improvements in neurocognitive function and diminution of constitutional symptomatology.

The present invention further describes intranasal therapy using Peptide T (for example, at dosage levels of about 1.2, 6, and 30 mg./day) in symptomatic HIV-infected humans over a six month period.

Furthermore, the invention relates to intranasal use of Peptide T to prevent, halt, and/or to reverse the immunological, virological and/or clinical manifestations of HIV infections as determined by monitoring clinical symptoms, frequency or severity of infections, disease progression, neurocognitive improvement, or serial T helper lymphocyte counts.

Additionally, the present invention relates to the treatment of Tropical Spastic Paresis (TSP) with Peptide T. Treatment of TSP is also accomplished by intranasal therapy using Peptide T. The treatment of TSP with Peptide T has resulted in substantial reversal of the symptoms associated with the disease e.g., paralysis of feet and legs. Improvements in bladder and sexual function were also observed as well as a decreased deterioration in memory and attention deficits.

SUMMARY OF THE INVENTION

It is an object of the present invention to provide peptides which would act to alleviate symptoms of AIDS by preventing binding of HIV (AIDS virus) to receptor sites of cells of brain membranes and the immune system.

It is also an object of the present invention to provide peptides for use as vaccines to protect against development of AIDS in persons who might become exposed to the HIV (AIDS virus).

It is a further object of the present invention to provide diagnostic means for identifying the presence of antibodies to HIV or HIV envelope protein.

An additional object of the present invention is the use of intranasal therapy using short peptide sequences which inhibit HIV as the active therapeutic ingredient.

A still further object of the invention is the use of Peptide T by intranasal administration for the treatment of symptomatic HIV-infected patients.

Another object of the instant invention is the therapeutic use of octapeptides and pentapeptides which inhibit HIV or gp 120 binding or toxicity to human cells.

A further object of the present invention are pharmaceutical formulations containing short peptide sequences useful for intranasal therapy of HIV infected patients.

Another object is to provide peptides which would act to alleviate the symptoms of other retroviral or viral diseases by preventing binding of the virus to receptor sites in the brain, body, or, immune system.

An additional object of the present invention is the use of short peptide sequences for the treatment of Tropical Spastic Paresis (TSP) as the active therapeutic ingredient.

A still additional object of the present invention is the use of Peptide T for the treatment of TSP.

Another object of the present invention in the use of Peptide T by intranasal administration for the treatment of TSP.

A further object of the invention is the therapeutic use of octapeptide and pentapeptides for the treatment of TSP.

A still further object of the present invention are pharmaceutical formulations containing short peptide sequences useful for intranasal therapy of TSP.

DETAILED DESCRIPTION OF THE INVENTION

An octapeptide in the HIV envelope glycoprotein (gp 120) was identified by computer-assisted analysis. This peptide, termed "peptide T" because of the high threonine content, has been shown to inhibit binding of gp 120 to the brain membranes. The peptide has the sequence Ala-Ser-Thr-Thr-Thr-Asn-Tyr-Thr. Later analysis disclosed a class of related pentapeptides having similar binding properties.

According to a first aspect of the present invention there is provided a peptide of formula (I);

$$R^a\text{-Ser-Thr-Thr-Thr-Asn-Tyr-}R^b \qquad (I)$$

where $R^a$ represents an amino terminal residue Ala- or D-Ala or Cys-Ala and $R^b$ represents a carboxy terminal residue -Thr, -Thr-amide, -Thr-Cys or -Thr-Cys-amide, or a derivative thereof, or a peptide of formula (II):

$$R^1\text{-}R^2\text{-}R^3\text{-}R^4\text{-}R^5 \qquad (II)$$

where $R^1$ is an amino terminal residue $XR^6$ or $R^6$ wherein $R^6$ is Thr-, Ser-, Asn-, Glu-, Arg-, Ile- or Leu- and X is Cys; $R^2$ is Thr, Ser or Asp; $R^3$ is Thr, Ser, Asn, Arg, Gln, Lys or Trp; $R^4$ is Tyr; and $R^5$ is a carboxy terminal residue which is $R^7X$ or $R^7$ wherein $R^7$ may be any amino acid and X is Cys, or a derivative thereof, with $R^5$ preferably being a carboxy terminal residue -Thr, -Arg or -Gly or a derivative thereof with a corresponding D- amino acid as the amino terminal residue. While the preferred amino acids at $R^5$ have been designated, it is known that the amino acid at this position may vary widely. In fact, it is possible to terminate the peptide with $R^4$ (tyrosine) as the carboxy terminal amino acid wherein $R^5$ is absent. Such peptides retain the binding properties of the group taught herein. Serine and threonine appear to be interchangeable for purposes of biological properties taught herein. The active compounds of the invention may exist as physiologically acceptable salts of the peptides.

This class of peptides has been found to bind to the HIV viral receptors, such as T4.

Most preferred peptides, as well as peptide T above, are the following octapeptides of formula (I):

D-Ala-Ser-Thr-Thr-Thr-Asn-Tyr-Thr, and

D-Ala-Ser-Thr-Thr-Thr-Asn-Tyr-Thr-amide;

and the following pentapeptides of formula (II):

Thr-Asp-Asn-Tyr-Thr,

Thr-Thr-Ser-Tyr-Thr, and

Thr-Thr-Asn-Tyr-Thr and their analogues with D-Thr as the amino terminal residue and/or an amide derived at the carboxy terminal.

The compounds of the invention may be beneficially modified by methods known to enhance passage of molecules across the blood-brain barrier. Acetylation has proven to be especially useful for enhancing binding activity of the peptide. The terminal amino and carboxy sites are particularly preferred sites for modification.

The peptides of this invention may also be modified in a constraining conformation to provide improved stability and oral availability.

The following abbreviations are used hereinafter:

| Amino Acid | Three Letter Code | One letter Code |
| --- | --- | --- |
| arginine | Arg | R |
| asparagine | Asn | N |
| aspartic acid | Asp | D |
| cysteine | Cys | C |
| glycine | Gly | G |
| serine | Ser | S |
| threonine | Thr | T |
| tyrosine | Tyr | Y |

Unless otherwise indicated the amino acids are, of course, the natural form of L-stereoisomers.

A comparison of amino acid sequences of 12 pentapeptides is presented in Table 1. Although historically our initial computer search revealed peptide T (contained in the ARV isolate) to be the relevant moiety, as additional viral sequences became available it became clear that the relevant, bioactive sequence, might be a shorter pentapeptide comprising, nominally, peptide T[4-8], or the sequence TTNYT. In the isolates we compared (Table 1) substantial homologies were discerned only in this, shorter, region. The majority of changes are the interconversions of serine (S) and threonine (T), two closely related amino acids. The tyrosine of position 7 of peptide T is an invariant feature of all these constructs indicating that it may be obligatory for bioactivity. Substitutions occurring at position 5 include T, G, R or S. Position 4 and 6 were first restricted (with one exception) to S, T and N, all amino acids containing uncharged polar groups with closely similar stearic properties. An assessment of general sequence concordance among 5 various AIDS viral isolates reveals that the region around and including the peptide T sequence is a highly variable area. Such variability may indicate specialization through strong selective diversification of the function(s) which may be defined at this locus. Like the opiate peptides, these peptide T analogs seem to exist in multiple forms, reminiscent of met and leu-enkephalin. These pentapeptide sequences represented in these various AIDS virus isolates are biologically active and capable of interacting as agonists of the CD4 receptor—previously known largely as a surface "marker" of T helper cells.

TABLE 1

Comparison of ENV Sequence from Multiple AIDS Virus Isolates

| Isolate | Sequence | Reference |
| --- | --- | --- |
| peptide T | ASTTTNYT | Pert, C.B. et al., PNAS (in press) |
| [1]ARV (195-199) | TTNYT | Willey, R.L. et al., PNAS 83: 5038, 1986 |
| LAV | TTSYT | |
| Z3 | SSTYR | |
| NY5 | TTSYT | |
| B10 (HTLV-III) | TTSYT | Starcich, B.R. et al. Cell 45: 637, 1986 |
| WMJ-1 | SSTYR | |
| HAT-3 | NTSYG | |
| Sequential isolates | STNYR | |
| WMJ-1 | SSTYR | Hahn, B.L. et al., Sciencve 232: 1548, 1986 |
| WMJ-2 | SSRYR | |
| WMJ-3 | SSTYR | |

[1]Numbers refer to relative positions of amino acids within the ARV env sequence (9).

The seven amino acid peptide CYS-THR-THR-ASN-TYR-THR-CYS is also active. Addition of cysteines to a core does not adversely affect activity nor does the inclusion of this core in a cyclic derivative or a peptide chain.

The peptides were custom synthesized by Peninsula Laboratories under a confidentiality agreement between the inventors and the manufacturer. The Merrifield method of solid phase peptide synthesis was used. (See U.S. Pat. No. 3,531,258 which is incorporated herein by reference.) The synthesized peptides are especially preferred. While peptide T and the pentapeptide which is a portion thereof could be isolated from the virus, the peptides prepared in accord with Merrifield are free of viral and cellular debris. Hence, untoward reactions to contaminants does not occur when the synthesized peptides are used.

The peptides that are to be administered intranasally in accordance with the invention may be produced by conventional methods of peptide synthesis. Both solid phase and liquid phase methods, as well as other methods e.g., enzymatic methods, may be used. We have found the solid phase method of Merrifield to be particularly convenient. In this process the peptide is synthesized in a stepwise manner while the carboxy end of the chain is covalently attached to an insoluble support. During the intermediate synthetic stages the peptide remains in the solid phase and therefore can be conveniently manipulated. The solid support is a chloromethylated styrene-divinylbenzene copolymer.

An N-protected form of the carboxy terminal amino acid, e.g. a t-butoxycarbonyl protected (Boc-) amino acid, is reacted with the chloromethyl residue of the chloromethylated styrene divinylbenzene copolymer resin to produce a protected amino acyl derivative of the resin, where the amino acid is coupled to the resin as a benzyl ester. This is deprotected and reacted with the next required amino acid thus producing a protected dipeptide attached to the resin. The amino acid will generally be used in activated form, e.g. by use of a carbodiimide or active ester. This sequence is repeated and the peptide chain grows one residue at a time by condensation at the amino end with the required N-protected amino acids until the required peptide has been assembled on the resin. The peptide-resin is then treated with anhydrous hydrofluoric acid to cleave the ester linking the assembled peptide to the resin, in order to liberate the required peptide. Side chain functional groups of amino acids which must be blocked during the synthetic procedure, using conventional methods, may also be simultaneously removed. Synthesis of a peptide with an amide group on its carboxy terminal can be carried out in a conventional manner, using a 4-methylbenzylhydroxylamine resin.

The compounds of the invention were found to effectively block receptor sites of cells and to prevent cell infectivity with HIV (AIDS virus) in monkey, rat and human brain membranes and cells of the immune system and to block the toxic effects of viral gp 120.

As an aspect of the invention, therefore, we provide a pharmaceutical compositions comprising a peptide compound of the invention in association with pharmaceutically acceptable carrier or excipient, adapted for use in human or veterinary medicine. Such compositions may be presented for use in a conventional manner in admixture with one or more physiologically acceptable carriers of excipient. The compositions may optionally further contain one or more other therapeutic agents which may, if desired, be a different antiviral agent.

Thus, the peptides according to the invention may be formulated for oral, intranasal, buccal, parenteral, topical or rectal administration.

In particular, the peptides according to the invention may be formulated for injection or for infusion and may be presented in unit dose form in ampoules or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, e.g., sterile, pyrogen-free water, before use. In a particularly preferred embodiment, the active ingredient may be administered intranasally, preferably in more than one daily application.

The pharmaceutical compositions according to the invention may also contain other active ingredients such as antimicrobial agents, or preservatives.

The compositions may contain from 0.001–99% of the active material.

The invention further provides a process for preparing a pharmaceutical composition which comprises bringing a peptide of the invention into association with a pharmaceutically acceptable excipient or carrier.

For administration by injection, nasal spray or infusion, the total daily dosage as employed for treatment of an adult human of approximately 70 kg body weight will range from about 0.2 to about 50 mg., typically from about 0.2 to about 30 mg, for example, from 0.2 mg to 10 mg. The total daily dosage may be administered in a single dosage application or in several dosage applications (e.g., 1 to 4 partial dosage applications), which combined, equal the total daily dosage, depending on the route of administration and the condition of the patient.

It was postulated that the affinity constants are similar to those of morphine. On the basis of this affinity, dosage of 0.33–0.0003 mg/kg per day was suggested. This has proven to be effective. A blood concentration $10^{-6}$ to $10^{-11}$ molar blood concentration is suggested. In monkeys 3 mg/kg per day achieves a serum concentration of $150 \times 10^{-9}$ M. This concentration is 15 times greater than necessary to achieve a concentration of $10^{-8}$ M. Primates generally require 10 times the dose used on humans.

A further aspect of this invention relates to vaccine preparations containing a peptide according to the invention, to provide protection against infection by AIDS virus. The vaccine will contain an effective immunogenic amount of peptide, e.g. 1 µg to 20 mg/kg of host, optionally conjugated to a protein such as human serum albumin, in a suitable vehicle, e.g. sterile water, saline or buffered saline. Adjuvants may be employed, such as aluminum hydroxide gel. Administration may be by injection, e.g. intramuscularly, interperitoneally, subcutaneously or intravenously. Administration may take place once or at a plurality of times, e.g. at 1–4 week intervals.

Antigenic sequences from crab as well as proteins from other invertebrates can also be added to the peptides of the invention to promote antigenicity.

A yet further aspect of this invention relates to test kits for the detection of the AIDS virus and antibodies to the AIDS virus containing a peptide according to the invention may be used in a test kit to detect AIDS infection and to diagnose AIDS and pre-Aids conditions by using it as the test reagent in an enzyme-linked immunosorbent assay (ELISA) or an enzyme immunodot assay. Such test kits may include an insoluble porous surface or solid substrate to which the antigenic peptide or monoclonal antibody has been preabsorbed or covalently bound, such surface or substrate preferably in the form of microtiter plates or wells; test sera; heteroantisera which specifically bind to and saturate the antigen or antibody absorbed to the surface or support; various diluents and buffers; labelled conjugates for the detection of specifically bound antibodies and other signal-generating reagents such as enzyme substrates, cofactors and chromogens.

The peptide according to the invention may be used as an immunogen to elicit monoclonal antibodies which specifically bind to the relevant portion of the envelope sequence of the AIDS virus, using conventional techniques; such monoclonal antibodies form a further feature of the invention.

A preferred embodiment of the present invention comprises delivery of the short peptide sequence by intranasal administration. The dosage levels of the peptides may vary, but generally are from about 0.2 to 50 mg./day, for example, about 1.2, 6 or 30 mg/day, given intranasally by metered spray, in three generally equally divided doses every eight hours. The use of peptide T has no toxic effect on blood cell counts, EKG, blood chemistries or urinalysis. Intranasal peptide T, according to the present invention is a safe therapeutic agent that is associated with stable CD4 counts, reduction of viral gp 120, with no clear cut effect on p24 antigenemia but reduced symptomatic and constitutional manifestations of HIV infection.

The peptides of the present invention were also found to be effective in the treatment of Tropical Spastic Paresis (TSP). TSP is a disease characterized by paralysis of feet and legs, there is bladder and sexual impairment, progressive deterioration as well as memory and attention deficits. The disease is endemic in tropical climates and southern Japan where approximately 200,000 people have the disease. TSP appears to be transmitted sexually as well as through human breast milk and is caused by a human retrovirus—HTLV I which is related to HIV, the AIDS virus (formerly called HTLV III). TSP is becoming more prevalent in the U.S. than previously believed as most likely a sexually transmitted disease. The disease is a nyclo-neurological degenerative disease.

The TSP or HTLV I virus has the peptide T-sensitive sequence in the viral envelope and as such peptide T has a broad spectrum anti-retroviral activity just like penicillin is a broad spectrum anti-bacterial of those bacteria with a similar cell wall (analogous to the viral envelope). Peptide T has been found to work on the neurons in the Sacral Spinal Cord that control the functions impaired in TSP disease.

The peptide of the present invention for treating TSP may be formulated for injection or for infusion and may be presented in unit dose forms in ampoules or in multidose containers as outlined above. In a preferred embodiment, the active ingredient may be administered intranasally, preferably in more than one daily application. The dosage levels of the peptides may vary, but generally are from about 0.2 to 50 mg/day, for example, about 1.2, 6 or 30 mg/day, given intranasally by metered spray in three generally equally divided doses three times a day and preferably every eight hours. The use of the above peptides and especially peptide T has no toxic effect on blood cell counts, EKG, blood chemistries or urinalysis. Intranasal peptide T, according to the present invention is a safe therapeutic agent for the treatment of TSP.

EXPERIMENTAL METHODS AND DATA

Radiolabeling of gp 120, Preparation of Brain Membranes, Binding and Crosslinking of gp 120 to Receptor, and Immunoprecipitation of T4 Antigen.

ETLV-IIIb isolate of HIV was propaged in H9 cells, and the gp 120 was isolated by immunoaffinity chromatography and preparative $NaDodSO_4$/PAGE. Purified gp 120 was labeled with 125 by the chloramine-T method.

Fresh human, monkey, and rat hippocampus were quickly homogenized (POLYTRON, Brinkmann Instruments) in 100 vol. of ice-cold 50 mM Hepes (pH 7.4). The membranes collected by centrifugation (15,000×g) were washed in the original buffer volume and were used fresh or stored at −70° C. Before use, brain membranes and highly purified T cells were preincubated for 15–30 min in phosphate-buffered saline (PBS). Preincubated membranes derived from 2 mg (initial we weight) of brain ($\alpha$100 µg of protein) were incubated with 28,000 cpm of $125_I$-gp 120 for 1 hour at 37° C. in 200 µl (final volume) of 50 mM Hepes containing 0.1% bovine serum albumin and the peptidase inhibitors bacitracin (0.005%), aprotinin (0.005%), leupeptin (0.001%), and chymostatin (0.001%). Incubations were rapidly vacuum-filtered and counted to determine the receptor-bound material.

Immunoprecipitation.

Immunoprecipitates were prepared by incubation (overnight at 4° C.) of 0.5% Triton X-100/PBS-solubilized, lactoperoxidase/glucose oxidase/$^{125}$I-iodinated brain membranes or intact T cells with indicated mAbs at 10 μg per reaction. A solid-phase immunoabsorbant (immunobeads, Bis-Rad) was used to precipitate immune complexes prior to their resolution by NaDodSO$_4$/PAGE. Control incubations contained no primary mAb or a subclass control mAb (OKT8).

Chemical Neuroanatomy and Computer-Assisted Densitometry.

Cryostat-cut 25-μm sections of fresh frozen human, monkey, and rat brain were thaw-mounted and dried onto gelatin-coated slides, and receptors were visualized as described. Incubations, with or without antibodies (10 μg/ml) against T4, T4A, T8, and T11, were conducted overnight at 0° C. in RPMI medium, crosslinked onto their antigens, and visualized with $^{125}$I-labeled goat anti-mouse antibody. Incubations of slide-mounted tissue sections to label the antigen-receptor with $^{125}$I-gp 120 were conducted in 5-ml slide carriers with (1 μM) or without unlabeled gp 120 or mAb OKT4A (10 μg/ml) (Ortho Diagnostics).

Separation of T-Lymphocyte Subsets.

Subsets of T cells were obtained by treatment of Percoll density-purified peripheral blood T cells with specific monoclonal antibodies (T4 or T8) at 10 μg/ml. The treated cells were then panned on a plastic Petri dish that was coated with goat [F(ab')$_2$] anti-mouse immunoglobulin (Sero Lab, Eastbury, Mass.) for 20 min at 4° C. The nonadherent cells were then removed, washed, and analyzed for reactivity by flow cytometry. The separated T4 and T8 cell populations have <5% contamination of other T-cell subsets. Cells were then cultured with phytohemagglutinin (1 μg/ml) for 72 hrs and exposed to HIV as described below. Infected cells were phenotypically characterized when cytotoxicity assays were performed.

Virus Infection.

The HTLV-III virus used for infection was isolated from an interleukin 2 (IL-2)-dependent cultured T-cell line established from fresh AIDS patient material and passaged into HuT 78, permissive IL-2-independent cell line.

Figure 2:
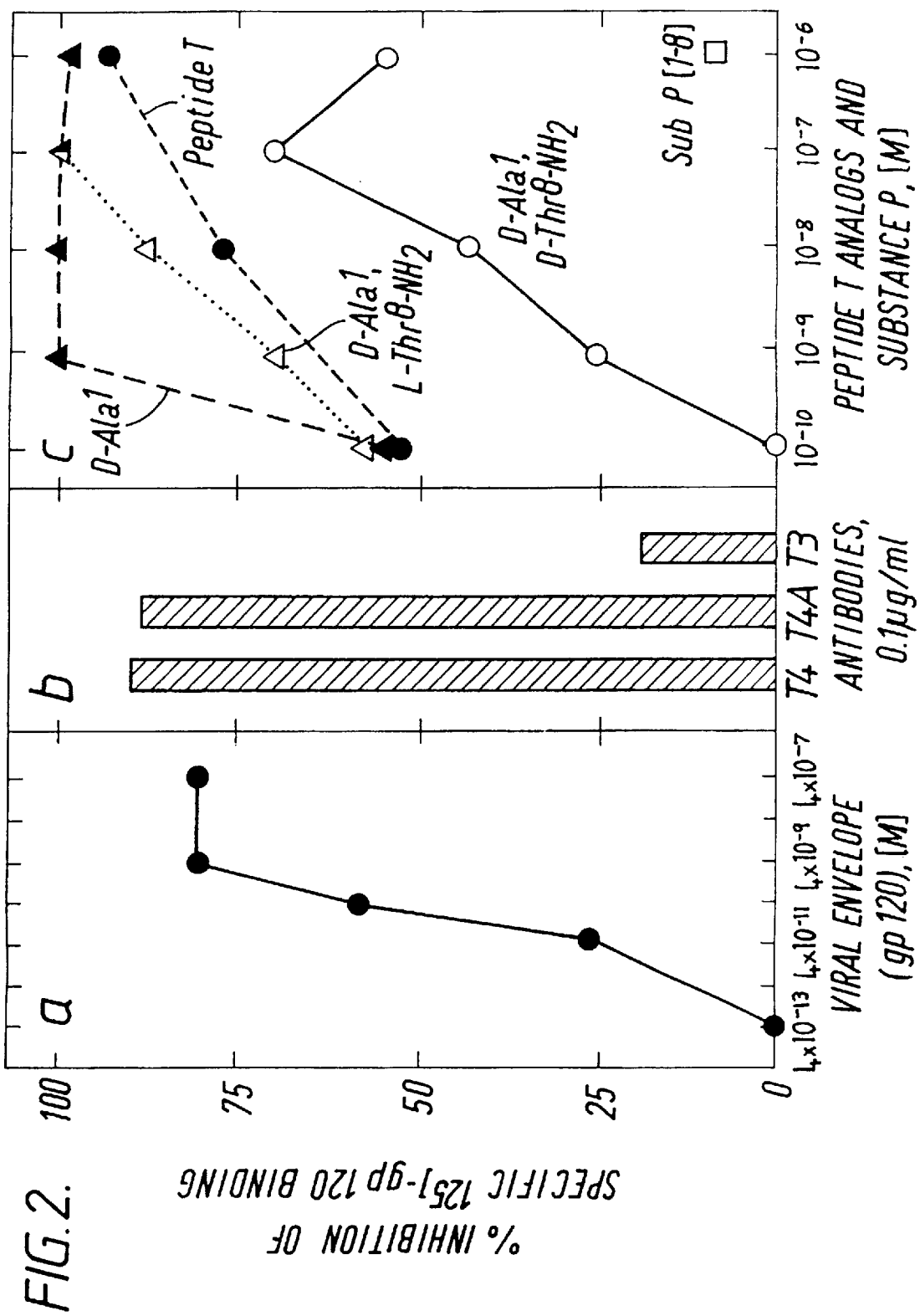

FIG. 2 shows a displacement of specific $^{125}$I-gp 120 binding (FIG. 2a) to fresh rat hippocampal membranes. Each determination was performed in triplicate; the results of one experiment, which was performed three times with similar results, is shown. Specific binding (FIG. 2b) displaceable by 10 μg/ml of OKT4 and 4A ranged between 27 and 85% of total binding, which was 2,201±74 cpm in the experiment shown. FIG. 2C shows that specific gp 120 binding is displaced by peptide T.

Figure 3:
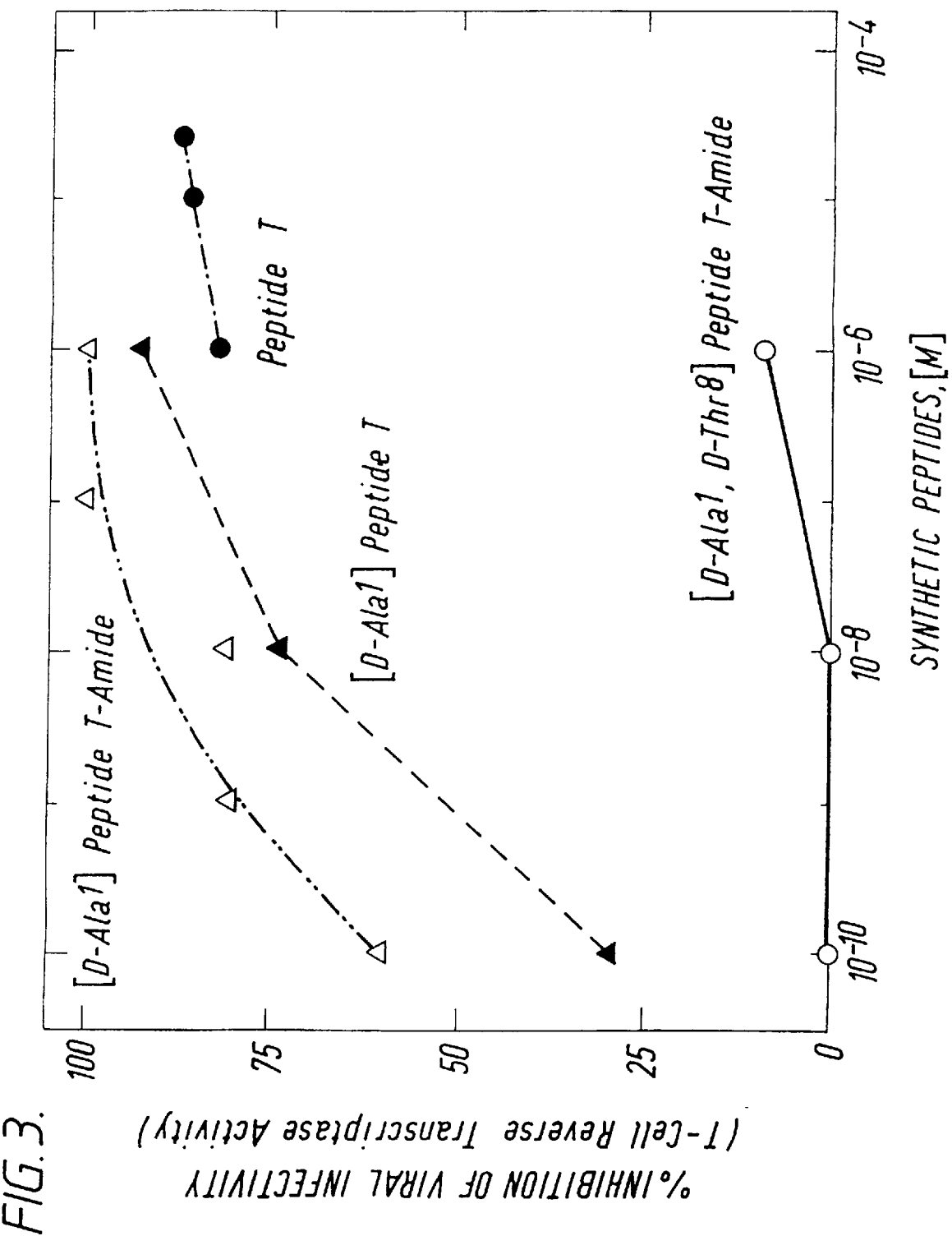

FIG. 3 shows that viral infectivity is blocked by peptide T and its synthetic analogs. Each determination was performed in duplicate. Results represent a single experiment which was repeated three times with similar results.

Figure 4:
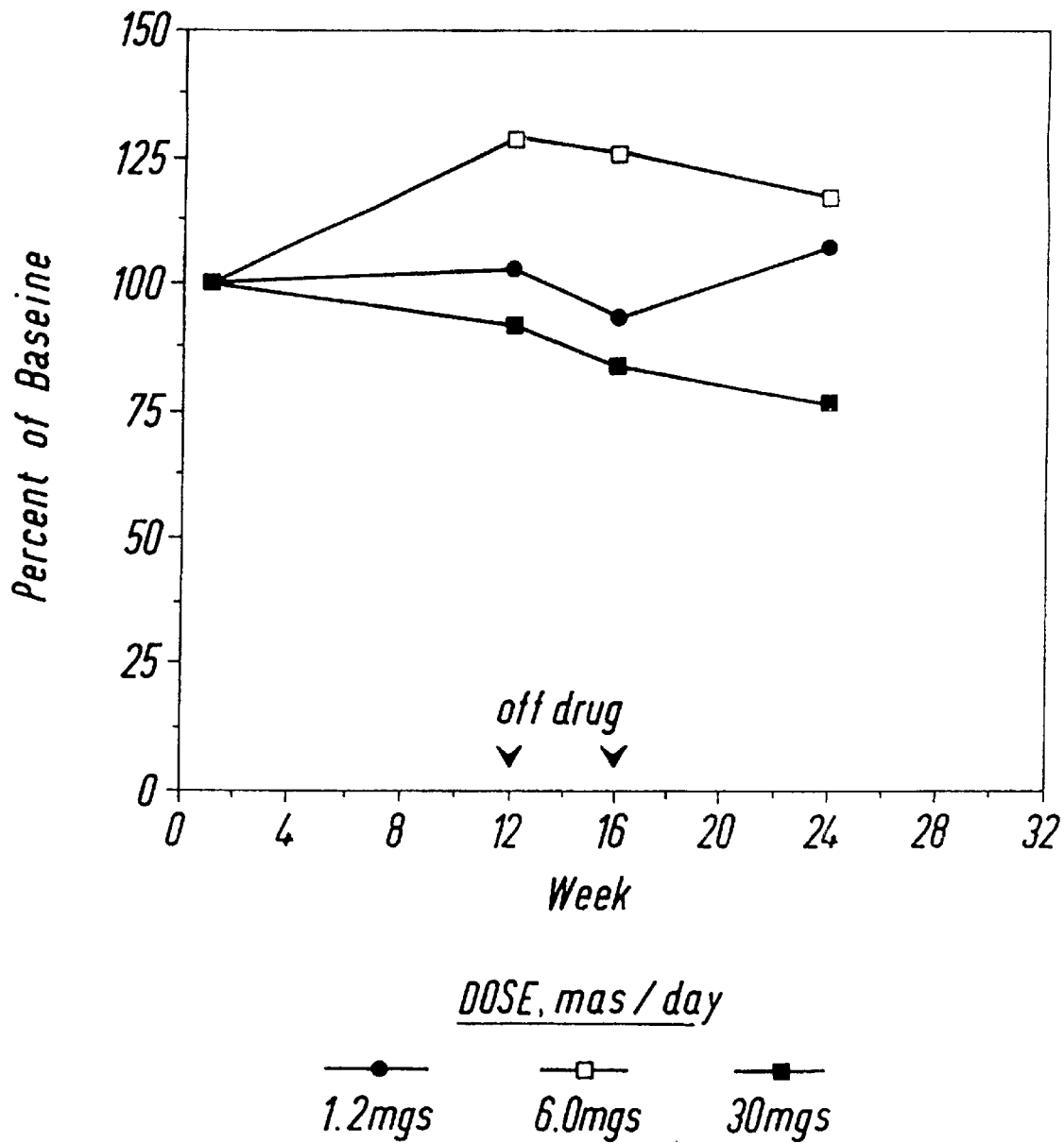

FIG. 4 shows the effect of dosage on the population of CD4 cells as a function of time.

EXAMPLE 1

Figure 1:
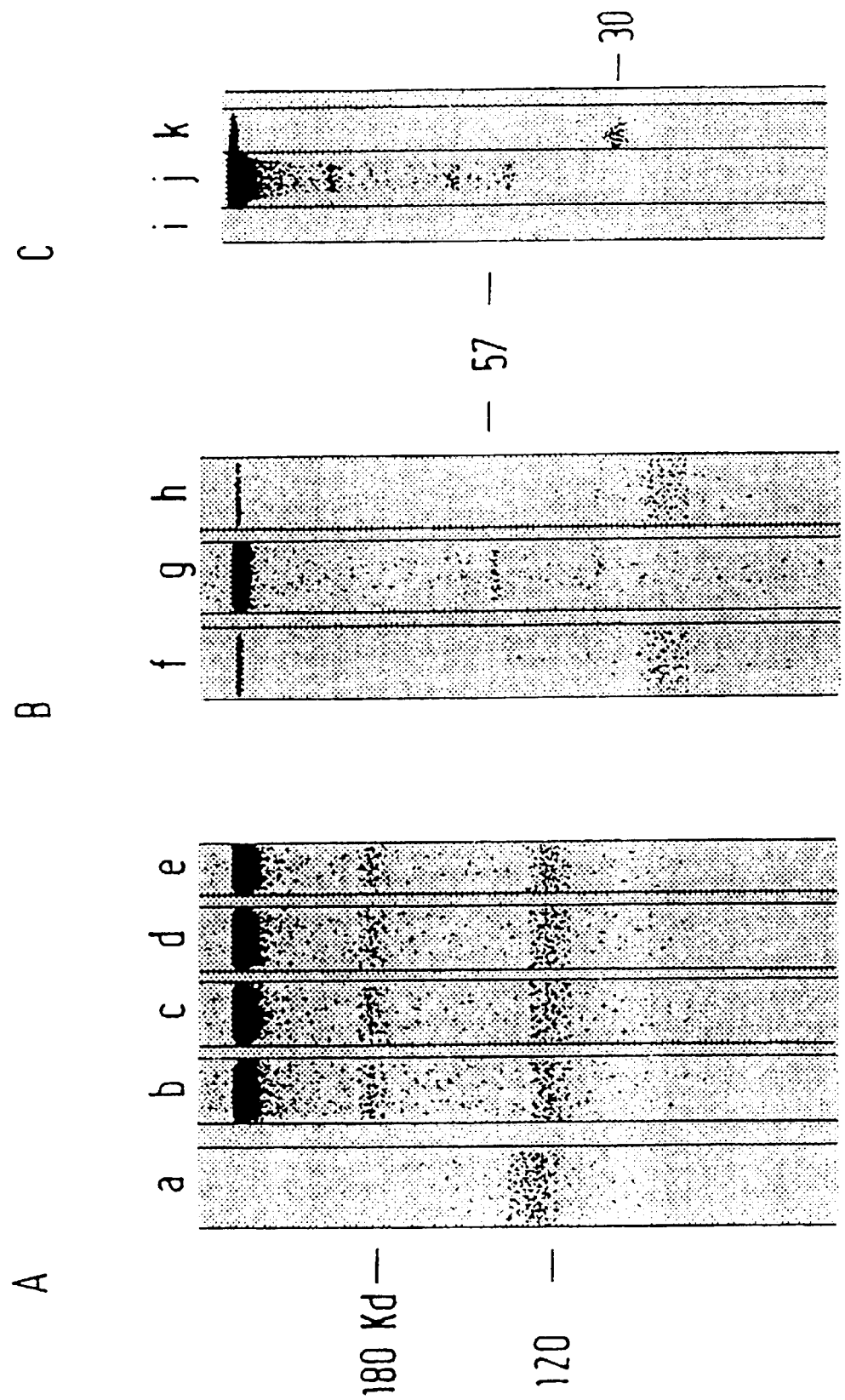
FIG. 1A shows a crosslinking of $^{125}$I-gp 120 brain membranes and T cells (a) $^{125}$I-gp 120 only; (b) monkey; (c) rat; (d) human brain; and (e) human T cells.
FIGS. 1B and 1C show immunoprecipitation of $^{125}$I-labeled monkey brain membranes and human T cells, respectively; (f,i) no primary antibody control (g,j) OKT4 Mab; (h,k) OKT8 Mab.

A single radiolabled crosslinking product of about 180 Kd is obtained after specific binding of $^{125}$I-gp 120 to membranes from either squirrel monkey, rat or human brain membranes which are indistinguishable from that of human T cells (FIG. 1A). This result indicates that gp 120 can be coupled to an approximately 60 Kd protein; unreacted $^{125}$I-gp 120 runs adjacent to the no membrane control (lane a).

Immunoprecipitation of radioiodinated human brain membranes with OKT4 and OKT8 (10 μg/ml (FIG. 1B) shows that brain membranes contain a T4 antigen of about 60 Kd, indistinguishable from that identified on human T lymphocytes (FIG. 1C); by contrast, OKT8 immunoprecipitates a low (about 30 Kd) molecular weight protein from T lymphocytes (FIG. 1C) which is absent in brain membranes (FIG. 1B) indicating that brain T4 is not derived from resident lymphocytes. Similar results are observed with monkey and rat (not shown) hippocampal membranes. These results show that the T4 antigen serves as the viral receptor and is a highly conserved 60 Kd molecule shared by the immune and central nervous systems.

The realization that Epstein-Barr and HTLV-III/LAV share an almost identical octapeptide sequence caused the synthesis and study of "peptide T." FIG. 2 demonstrates the high (0.1 nM range) affinity and saturability (FIG. 2a) of $^{125}$I-gp 120 binding to freshly prepared rat brain membranes. Specificity (FIG. 2b) is demonstrated by blockade with OKT4 and OKT4A, but not OKT3 (0.1 μg/ml). Peptide T and two of its synthetic analogs (but not the irrelevant octapeptide substance P [1-8]) significantly inhibited $^{125}$I-gp 120 binding in the 01.1 nM range (FIG. 2c). Substitution of D-threonine-amide in position 8 resulted in at least a 100-fold loss of receptor binding activity. The classical [D-Ala] substitution for [L-Ala] results in a consistently more potent, presumable more peptidase-resistant, analog than peptide T; amidation of the C terminal threonine also consistently produces somewhat greater potency (FIG. 2c).

When the synthetic peptides were tested for their ability to block viral infection of human T cells, experimenters were blind to binding assay results. At $10^{-7}$M the three peptides active in the binding assay are able to reduce detectable levels of reverse transcriptase activity by almost 9-fold. The less active binding displacer [D-Thr]$_8$-peptide T similarly showed greatly reduced blockade of viral infection, requiring concentrations 100-fold higher to achieve significant inhibition. Thus, not only the rank order of potencies of the four peptides (D-[Ala]$_1$-peptide T-amide>D-[Ala]$_1$-peptide T>peptide T>D-[Thr]$_8$-peptide T-amide), but also their absolute concentrations in inhibiting receptor binding and viral infectivity are closely correlated (FIGS. 2c, 3).

EXAMPLE 2

An approximate 60-kd protein, which is similar if not identical to human T cell T4 antigen, was present in apparently conserved molecular form on membranes prepared from human brain; furthermore, the radiolabled HIV envelope glycoprotein ($^{125}$I-gp 120) can be covalently crosslinked to a molecule present in three mammalian brains whose size and immunoprecipitation properties were indistinguishable from the T4 antigen. Using a method for visualizing antibody-bound receptors on brain slices, the neuroanatomical distribution pattern of brain T4, which is densest over cortical neuropil and analogously organized in all three mammalian brains, was presented. Also, radiolabeled HIV viral envelope glycoprotein bound in an identical pattern on adjacent brain sections, once again suggesting that T4 was the HIV receptor in brain.

EXAMPLE 3

Chemical Neuroanatomy, Computer-Assisted Densitometry. Cryostat-Cut 25 micron sections of fresh-frozen human, monkey, and rat brain were thaw-mounted and dried onto gel-coated slides and receptors visualized as described by Herkenham and Pert, *J. Neurosci.*, 2: 1129–1149 (1982). Incubations, with or without antibodies (10 μg/ml) against T4, T4A, T8 and T11, were conducted overnight at 0° C. in RPMI, crosslinked onto their antigens and visualized with $^{125}$I-goat anti-mouse antibody. Incubations of slide-mounted tissue sections in order to label antigen/receptor with $^{125}$I-gp 120 were conducted in 5 ml slide carriers with ($10^{-6}$M) or without unlabeled gp 120 or Mab OKT4A (10 μg/ml) (Ortho Diagnostics) as described above for membranes.

Computer-assisted transformation of autoradiographic film opacity into quantitative color images was performed. Co-exposure of standards of known increments of radioactivity with the monkey brain sections generated a linear plot (4=>0.99) of log O.D. versus cpm from which the relative concentration of radioactivity can be meaningfully extrapolated. Cell staining of brain sections with thionine was performed by classical methods and visualization of receptors overlying stained tissue.

EXAMPLE 4

Experiments have been conducted to determine the distribution of T4 antigen on a rostral to caudal series or coronal sections of squirrel monkey brain. These experiments show that there are detectable levels of T4 monoclonal antibody binding to cytoarchitectonically meaningful areas of the brain stem (e.g., the substantia nigra), but the striking pattern of cortical enrichment is apparent at every level of the neuroaxis. OKT8, a T-lymphocyte directed monoclonal antibody from the same subclass as OKT4, exhibits no observable pattern. Generally, the more superficial layers within the cerebral cortex contain the densest concentrations of the T4 antigen; the frontal and perilimbic cortex overlying the amygdala are particularly receptor-rich throughout the deep layers. The hippocampal formation has the densest concentration of receptors in the monkey, rat, and human brain. Dark field microscopy of squirrel monkey sections dipped in photographic emulsion revealed that the band of densest receptor labelling is located within the molecular layers of the dentate gyrus and hippocampus proper (which contain very few neurons). Thus, receptors appear to be rightly distributed over the neuropil (the neuronal extensions of dendrites and axons) or may be localized to a specific subset of unstained astroglial cells.

Evidence of the specificity of the chemical neuroanatomy and results showing that T4 and the viral envelope recognition molecule are indistinguishable has been determined. Coronal sections of rat brain revealed a very similar cortex/hippocampus-rich pattern of receptor distribution whether OKT4 or $^{125}$I-gp 120 was used for visualization. Furthermore, this pattern was not apparent when incubation occurred in the presence of unlabeled gp 120 (1 μM), OKT4A (10 μg/ml) or OKT4 (10 μg/ml). Other mouse Mabs directed against other human T cell surface antigens including OKT8 and OKT11 gave no detectable pattern on rat brain when visualized by $^{125}$I-goat anti-mouse IgG secondary antibody just as there was no reproducible. Detectable antigen/receptor with secondary antibody alone.

METHODS FOR INTRANASAL THERAPY

Preparation, Pharmacology and Pharmacokinetics:

According to GMP practices, Peptide T was made by automated solid phase peptide chemistry, purified by high performance liquid chromatography (HPLC), and purity was assessed by thin layer chromatography and analytical HPLC (Peninsula Labs, Belmont, Calif.). Peptide T is stable in pharmaceutical form at room temperature for greater than three months, and in dry form for more than one year. Analytical HPLC indicated that Peptide T was >95% pure. The Peptide T used in this study was prepared freshly from powder using a neutral vehicle of 0.15M NaCl with 0.9% benzylalcohol as a preservative by the Pharmaceutical Development Service of the National Institutes of Health under contract with the National Institute of Mental Health. The placebo vials contained the neutral vehicle without Peptide T. Intranasal drug was delivered by a metered sprayer at the three study doses via two sprays of 0.1 ml each per nostril given on a t.i.d. basis based on data obtained in previous studies.

The pharmacokinetics of D-Ala$_1$-peptide-T-NH$_2$ (peptide T) was determined during phase I clinical trials in patients with acquired immunodeficiency disease (AIDS) and AIDS related complex (ARC). In this invention drug levels were determined by specific RIA, and in some cases with HPLC analysis, after an intravenous (i.v.) test dose or intranasal (i.n.), via metered sprayer administration.

Study Measurements and Follow-Up:

After signing the appropriate informed consent approved by the Fenway Community Health Center Institutional Review Board, participants were seen weekly for the first two weeks of the study and subsequently every two weeks. Routine laboratory tests obtained during the trial included: electrolytes, renal and hepatic function tests (SMA-18), complete blood count and differential, and urinalyses. Less frequent monitoring included chest x-ray, electrocardiogram and random urine drug screening for alcohol, opiates and other neuroactive compounds. Cutaneous anergy was assessed using the Merieux Institute Panel every six weeks; T lymphocyte subpopulations were evaluated after three, four and six months on Peptide T as was serum p24 antigen. Participants underwent a routine review of symptoms and physical exam, as well as thorough neuropsychological testing. Ten symptoms, identified as common constitutional symptoms of HIV infection were analyzed for by prevalence and severity in the course of the study (Table One). Symptoms were coded as not present (1), mild (2), moderate (3), severe (4), and life threatening (5). Participants were surveyed at baseline and each subsequent visit. These key symptoms were analyzed by Repeat Measured Analysis of Variance (ANOVA) and tests for interactions between these variables. The choice of neuropsychological tests was based on data from earlier studies. Computerized EEG testing was performed on all participants at entry and lumbar puncture examination of cerebrospinal fluid was performed in individuals whose signs and symptoms suggested active clinical neurological impairment or a rapid change in neurocognitive function.

Study Design For Intranasal Therapy.

This single-blind study randomized 32 patients with symptomatic HIV infection (CDC IV classification) and CD4 counts on two successive determinations between 100 and 500 cells/mm$^3$ to receive one of three randomly assigned dosage levels of intranasal Peptide T for 12–16 weeks (1st phase) followed by four weeks off-drug in which patients received an intranasal inhaler containing the vehicle fluid but no Peptide T (2nd phase), and an addition eight weeks in which patients received active drug in the inhaler (3rd phase).

Drug dosage levels were 1.2, 6 and 30 mg/day, given intranasally by metered spray, in three equally divided doses every eight hours. Eleven patients received 1.2 mg/day (low)

12 patients received 6 mg/day (medium) and nine patients received 30 mg/day (high dose).

All patients received an initial intravenous test dose of 0.033 mg/kg of Peptide T for the pharmacokinetics studies. The test dose was administered over one hour in 100 cc of D5W, followed by an observation period of six hours. Additional samples where taken 24 and 48 hours after the test dose. Patients received their first intranasal dose 72 hours after the IV dose and blood samples were taken at identical times after administration. Study clinicians and neuropsychological testers were blind to drug dose and timing of the placebo. All participants signed an informed consent in which they agreed to not take any other antiviral or immunomodulatory drugs during the course of this Phase I study.

Results of Intranasal Study

Adverse Experiences: No hematologic, hepatobiliary, or renal toxicities were attributable to Peptide T. No clinically meaningful electrocardiographic changes were noted. Two participants developed maculopapular rashes during the trial. Both rashes resolved with discontinuation of antibiotic (amoxicillin-clavulanic acid; trimethoprim-sulfamethoxazole). Twenty-five participants reported occasional increased nasal congestion accompanied by boggy, erythematous mucosa. Three participants had epistaxis or discomfort which let to temporary drug discontinuation for less than 48 hours. Two developed sinusitis which promptly responded to antibiotics. Eleven participants had symptom relief with nasal decongestant sprays, over-the-counter oral decongestants, or experienced spontaneous resolution after temporary discontinuation. Pharmacokinetics monitoring studies confirmed that nasal congestion did not impair adequate drug absorption.

Clinical Outcomes:

Of 32 participants enrolled in the study, 8 were discontinued from the trial. Four participants developed major opportunistic infections (OI) during the study (see Table 2 below). Two of these participants developed OI during the placebo phase, but premonitory symptoms were present while on the drug. The individual with MAI probably had active, but not clinically evident disease prior to beginning Peptide T. Although one patient withdrew from study due to probable antibiotic skin rash, a second patient with similar symptoms was rechallenged with Peptide T and Pharmacokinetics:

Plasma kinetics appeared to be biphasic with a first compartment half-life of 30 to 60 minutes and a second plasma clearance rate of 4 to 6 hours, observed for both routes of administration (Table 3). Bioavailability, determined for the 2 mg dose in six individuals was 9.3±6.9 nmol/L. Peak plasma levels of 41±30 nmol/L after 10 mg, 2.8±5.9 nmol/L after 2 mg, and 0.13±0.07 nmol/L after 0.4 mg i.n. were observed. Peptide T has been detected in CSF at levels 20% of the corresponding plasma level after i.v. administration. Peptide T was not detected in urine.

TABLE 3

PHARMACOKINETIC PROPERTIES OF INTRANASAL PEPTIDE T

| | DOSE | | |
|---|---|---|---|
| | 10 mqs* | 2 mqs* | 0.4 mqs# |
| T½(MIN) | | | |
| 1ST COMPARTMENT | | 30–60 MIN | |
| 2ND COMPARTMENT | | 4 TO 6 HRS | |
| PEAK PLASMA | | | |
| CONCENTRATION | 3.4 e-8m | 2.8e-9m | 1.3e-10M |
| BIOAVAILABILITY | 2.9 ± 1.5% | 1.2 ± 2.2% | 21 ± 11% |

*ENTRY REPRESENTS THE MEAN OF SIX (#FIVE) PATIENT MEASUREMENTS BY RIA (23).

Key Symptoms:

Eight symptoms that were systematically assessed at each visit were identified for statistical comparisons as potential indices of progressive HIV infection (Table 4). The analyses were complicated by the fact that these symptoms were not invariably present at baseline for all participants. One participant who covertly added zidovudine to his regimen is not included in these analyses. At any time during the course of the trial, participants may have manifested any one (or all) of the symptoms at various levels of severity or may not have manifested any. Thus, the percentage of participants manifesting the symptom at baseline as compared to the percentage of participants manifesting the symptom during the continuous treatment phase.

ANOVA testing was performed to estimate whether independent dose and time effects on symptom report were observed. Because participants were stratified for dose by either the presence for severity of symptoms, all ANOVA covary for entry score on each symptom. Participants were

TABLE 2

PARTICIPANTS NOT COMPLETING FULL STUDY (24 WEEKS)

| S # | WK D/C | DOSE Mq/d | REASON | WHILE ON PLACEBO |
|---|---|---|---|---|
| 002 | 6 | 6 | *M. AVIUM INTRACELLULARE* INFECTION | NO |
| 004 | 6 | 1.2 | RASH, PROBABLY DUE TO CONCURRENT ANTIBIOTIC | NO |
| 005 | 14 | 1.2 | P. CARINII0 PNEUMONIA | NO |
| 009 | 14 | 1.2 | P. CARINII0 PNEUMONIA | YES |
| 018 | 14 | 1.2 | P. CARINII0 PNEUMONIA | NO |
| 024 | 8 | 30 | WITHDREW TO TAKE AZT | NO |
| 030 | 20 | 6 | WITHDREW TO TAKE AZT | NO |
| 033 | 22 | 1.2 | WITHDREW TO TAKE AZT | NO | completed the study. Other outcomes included the development of thrush (n=2), recurrences of herpes simplex (n=2), and an initial case of oral hairy leukoplakia (n=1). Three participants withdrew from study in order to receive nucleoside analog antiretroviral therapy.

aware that they began on active drug at the outset of the study, but were unaware of either the timing or length of the placebo period. In order to minimize the effect that all participants knew they began on active drug, the analysis examined each protocol condition period separately. Table 4 summarizes the major associations of symptom changes in the course of the study as a function of dose and timed independently and in an interactive manner.

As can be seen in Table 4, there are time effects present for many symptoms throughout the study, independent of dose. In general, dose effects or dose/time interactions did not appear during the first on drug period. Dose effects occurred where one dose was associated with significant change in a symptom reporting. During the placebo period, dose effects occurred where there was a fit to the study design (i.e., a worsening in symptom scores associated with a particular dose) or where continued improvement was associated with a specific dose. Fatigue scores worsened for the lowest dose and fever scores worsened for the highest dose during the placebo period.

During the second on drug period, there were time effects independent of dose for improved ability to concentrate and for reduction of fatigue. Dose effects or time/dose interactions were present for improved scores for fever, night sweats, and confusion. These dose effects were all present for the lowest dose (1.2 mg/day). Because most of the dose effects represented trends rather than achieving significance ($p<0.05$), statistical power for detecting differences in these symptoms was calculated. These calculations indicate that assuming similar effect size, a sample of 50 subjects would be required. The mean score change for the symptom with the greatest baseline prevalence (e.g. fatigue) and, therefore, greatest opportunity for improvement, demonstrated the greater mean change on study. Similarly, the symptoms with the least prevalence at baseline (e.g. confusion, night sweats, fever, depression) demonstrated the least overall mean change on study.

indicated that 9 patients demonstrated normal EEGs but 12 were abnormal. CEEGs suggested a pattern of significant slowing and seizure-like potentials. Similarly, brain mapping studies indicated more slowing in the more advanced patients, predominantly in anterior and temporal brain areas, compared to historical aged-matched controls. After Peptide T, most of the patients demonstrated a slight to moderate increase of alpha activity with a decrease of slow delta activity, seen with other neurotropic and anti-dementia drugs. In some patients, Peptide T decreased spikes and sharp waves.

Weight.

Weight was stably maintained for the majority of participants throughout the study. Of six participants who were discontinued as a result of opportunistic infections or at their request, all but one showed weight reductions.

T Lymphocyte Subpopulation Studies:

Twenty-nine participants who had more than one T lymphocyte subset determination were included in analysis of the changes in T4 and T8 cells in the study. Because of the variability in the number of T helper cells per individual determination, the mean CD4 and CD8 counts of the two visits prior to receiving drug were used as the baseline value for the numbers of specific T cells.

Split-plot analysis of the data showed stabilitation of T4 cell/ene (FIG. 4). The mean initial CD4 count was 284 cells/mm$^3$ (range 108–476) at entry into the study at 294 at six months (range 60–625). T4 data were analyzed by dose group, as seen in FIG. 4. Although there was some variation consistent with the on-off-on protocol in the low dose group, these values were not statistically different from the other two groups. The mean changes on and off Peptide T were

TABLE 4

CHANGES IN KEY SYMPTOMS DURING 24 WEEKS OF PEPTIDE T:
TIME- AND DOSE-ASSOCIATED INTERACTIONS*

| SELF-REPORTED SYMPTOM | PREVALENCE (%) | | SIGNIFICANT IMPROVEMENT SEEN IN RELATION TO: | | |
|---|---|---|---|---|---|
| | AT BASELINE | BY 24 WEEKS | TIME | DOSE | TIME-DOSE INTERACTION |
| FATIGUE | 90 | 65 | + | TREND | |
| MEMORY LOSS | 55 | 35 | + | | |
| DIARRHEA | 52 | 27 | TREND | | |
| INABILITY TO CONCENTRATE | 48 | 21 | + | | |
| CONFUSION | 29 | 27 | TREND | TREND | |
| DEPRESSION | 28 | 15 | + | | |
| NIGHT SWEATS | 26 | 21 | + | | TREND |
| FEVER | 23 | 11 | | TREND | |

*ANOVA OF REPEATED MEASURES (26); SEE TEXT FOR MORE DETAIL.
+ = $p < .05$;
TREND = $P < 0.1$

Objective neuropsychologic tests demonstrated improvement in cognitive and motor function consistent with the dose effects observed here. One patient experienced a reduction in painful sensory neuropathy consistent with the on-off-on pattern of the study.

Computerized Electroencephalogram (CEEG):

Twenty-one patients from this study were evaluated for deviations from normal in EEG and CEEG. Additionally, the effect of intranasal Peptide T administration on reversal of abnormal findings was studied. Patients were treated with Peptide T at doses of 1.2 mgs (n=10), 6 mgs (n=8), and 30 mgs (n=5) per day for 12 weeks. Conventional EEG testing generally less than 25% of baseline CD4 counts making interpretation difficult given the variability of reported CD4 counts in untreated HIV-infected subjects. Some individuals within this group did show pronounced increases in T4 cells. Untreated, HIV patients, whose illness was as advanced as this cohort, typicall show declines in T4 cells by six months compared to baseline.

As with CD4 lymphocytes, continuous treatment with Peptide T in doses of 1.2 or 6 mg/day was associated with stable numbers of CD8 cells in the course of the trial. A slight, but not significant, reduction in CD8 levels was noted over time among those participants who received 30 mg/day.

The relationship between CD4 and CD8 counts and the progression of HIV diseases was unclear in this study. Six participants who had large reductions (>100 CD4 cells/mm$^3$) in the number of CD4 cells completed the trial without developing opportunistic infections or other new clinically significant symptomatology. On the other hand, determination of the number of CD4 lymphocytes of participants who developed opportunistic infections after three months of Peptide T revealed that one had increased numbers of cells; the number of T4 helpers of the second were unchanged and a third had a declining CD4 count at his final visit.

Serum:

p24 antigen:

p24 antigenemia ($\geq$10 pcg/ml) was present in nine participants at baseline (mean: 121 pg/ml, range 8–468 pcg/ml), three of whom became p24 Ag negative and one had reduced levels (less than 30 pcg/ml) over the course of the trial. The mean titer for the six who were still antigenemic after 24 weeks was 58 pg/ml. Three of the participants whose p24 Ag titers were initially undetectable became antigenemic while on Peptide T treatment, and titers increased in four participants after 24 weeks. Changes in the presence of p24 Ag and the magnitude of the levels did not correlate with the development of major or minor opportunistic infections, or other parameters of clinical status.

Treatment of TSP with Peptide T

In a preliminary and unblinded study, 3 patients with TSP were given Peptide T for 10 weeks. HTLV-1, but not HIV antibodies were present in the serum and CSF of all three patients. Patient 1 was a male, age 63, who had progressive gait ataxia for 9 years associated with postural hypotension. Patients 2 and 3 were female, both age 59 with a 9 year history of progressive spastic paraparesis. All patients were ambulant. A plastic aerosol system, containing 5 mg/ml of a Peptide T solution was provided and about 6 mg administered each day, via four metered intranasal sprays 3 times daily. Patients were reviewed at monthly intervals and videotaped. No side effects were observed. Patients 1 and 2 showed no substantial changes in symptoms and were timed over 10 meters at 166 and 19.5 initially, and 227 and 16.5 seconds respectively at the end of week 10. Patient 3 reported substantial improvement which began in week 2 and continued to the end of week 10. She took only 15 seconds to walk 10 meters at this time, compared to 65 seconds initially. Four weeks after treatment was stopped, stiffness in her legs returned. As can be seen from the above limited trial, Peptide T is a non-toxic therapeutic modality that is easily administered, and has a beneficial effect in some patients with TSP.

Another patient 4, a longterm symptomatic woman was treated similarly as above, and return of bladder control and ability to walk and climb was achieved within 12 weeks as a result of Peptide T therapy.

Discussion of Intranasal Therapy Using Peptide T:

Although nucleoside analogues have been shown to be efficacious in delaying HIV-associated immunocompromise in individuals with CD4 counts<500, toxicity and clinical failure may be seen. In many of the initial studies, surrogate markers such as CD4 counts have shown initial amelioration in the first one to two months of receiving antiretroviral therapy. By six months, however, CD4 counts have tended to return to or below their baseline levels. Current studies are under way in an attempt to see whether antiviral combinations or antiviral plus immunomodulators either increase efficacy or reduce toxicity.

Preliminary studies with Peptide T have suggested neurocognitive improvement and/or constitutional symptom amelioration in HIV-infected patients. T helper lymphocyte counts remained stable in several dosage groups for six months. Some individuals showed increases. There was a slight but non-significant increase in T helper lymphocytes at three months in the middle range group. Failure to note systematic increases in CD4 counts, a primary marker of HIV progression, could be interpreted as evidence of absent antiviral effect. It can be noted that these are advanced HIV infected persons (CDC IV) with CD4 counts<500. Untreated disease progression in this time frame would likely be associated with substantial decrements of CD4 counts in this sample. Moreover, data from studies of drugs found to be effective as antiviral produces similar CD4 results in a 6 month time frame.

There was a reduction in overall reported symptomatology during the course of the study in all symptoms surveyed. Interpretation of this effect was confounded, since participants were aware that they began on active drug, hence there was a possibility that Hawthorne effects could have influenced self-reporting of symptoms. In fact, such a phenomenon may have adversely affected the possibility that dose effects, seen later in the study, would emerge during the first phase of the protocol. Because the participants were unaware of the duration or sequence of the placebo period, the second on drug period is probably the more reliable period to assess self report symptoms. In this last eight week period, there are dose effects for four of ten symptoms assessed. Interestingly, these are the more constitutionally-based (fever, night sweats, and rash) symptoms rather than mood-weighted symptoms (depression, headache, inability to concentrate, insomnia). Where present, dose effects were more likely to be associated with the lowest dose tested in this study (1.2 mg/day).

Peptide T is associated with improved cognition and the reduction of HIV-associated symptomatology reported here. The potential differential effect of Peptide T centrally and peripherally may be due to myriad reasons, including: 1) different effects of Peptide T at VIP or other receptors centrally and peripherally; 2) different time course of central and peripheral effects of Peptide T; 3) different concentrations for agonist properties of Peptide T centrally and peripherally; or 4) modification by Peptide T of central systems associated with cognitive neuromotor improvement without peripheral anti-HIV benefit.

The expression of p24 antigenemia is generally a late stage phenomenon of HIV infection, however, the prognostic utility of p24 antigenemia has been questioned. It is not clear that Peptide T would ever have an effect on p24 antigenemia. If Peptide T does exert some agonist activity peripherally leading to CD4 stabilization, it is not likely that such an effect would necessarily lead to reduced viral core protein production among already infected cells. Peptide T could also provide some trophic benefit at a receptor level, but not have effect on virion or viral core protein production. There were no deaths and a low number of infections in patients receiving peptide T.

Thus, the data presented with this invention suggest that Peptide T acts at a site different from nucleoside analogues. It is possible therefore, that Peptide T may act synergistically with the nucleoside analogues to provide benefit in cognitive, neuromotor, anti-viral and symptom areas, as well as being effective in its own right. Studies are now under way to assess this possibility and to refine the possible role of Peptide T in HIV infection.

In the data of the present invention, no clear-cut Peptide T-related toxicities were noted, and several of the participants reported marked improvement in constitutional symptomatology, energy, malaise, as well as objective neurocognitive functioning. About half of the cohort who continue to take peptide T have remained stable on Peptide T for almost two years in an expanded access protocol, without any new toxicities noted. They have been able to add other anti-HIV medications such as zidovudine without discernable untoward effects.

According to CEEG/Dynamic Bran Mapping results, the following effects were observed as a function of dosage:

Low Dosage of Peptide-T (1.2 mg)

This group of 10 subjects show predominant alpha activities, with a high percentage of alpha in posterior areas, which remained the same after Peptide-T treatment. The dosage of 1.2 mg. produced no significant effect in predominant activities. However, secondary activities slight but definite changes. For example, there was a decrease of theta in the posterior and temporal brain areas, and theta was replaced by beta activity. The extensive spread of theta in the anterior brain areas was lessened after treatment of Peptide-T.

Moderate Dosage of Peptide-T (6.0 mg)

This group of subjects shows predominant alpha activity with high percentage in the occipital areas before treatment. The predominant activity in anterior temporal areas was theta activity. After Peptide-T treatment, temporal theta was significantly reduced and was replaced by beta activity. The extension of high percentage alpha activity significantly increased, particularly in right parietal and posterio-temporal areas. As secondary activities this group of subjects showed, in all brain areas, theta except in the left anterio-temporal (alpha activity). A marked decline in theta activity after Peptide-T treatment was observed. Beta activity replaced theta, particularly in frontal and posterior brain areas. In temporal brain areas, a definite increase in alpha activities wa seen.

High Dosage of Peptide-T (30.0 mg)

A predominance of alpha in EEG with a high percentage of alpha in posterior areas. After Peptide-T treatment, with a slight increase of percentage in left anterio-temporal areas were observed, however, high percentage of alpha showed slight decrease. In secondary activities this group showed predominant theta EEG, with slight beta in left posterior temporal. After Peptide-T treatment, a decrease of theta, particularly in tempor-occipital area which is replaced by beta. Left anterior temporal shows activities.

The CEEG/Brain Mapping indicates:
A) All three groups of A.I.D.S. patients have predominant alpha and secondary theta activities in their EEG before treatment. After Peptide-T treatment, independent of dose, theta activity decreased, beta and alpha activities increased. These changes are seen most in the temporal and occipital areas.
B) The most C.N.S. effective dose of Peptide-T compositions tested appears to be 6.0 mg. Although 30 mg also has theta decreasing effects, the alpha activity was not increased. 1.2 mg seems to be less effective than 6.0 mg, but 30 mg was not proportionately quantitatively and qualitatively more effective than 6.0 mg of Peptide-T treatment (one has to consider, however, the sample size with 30 mg was only n=5)
c) The invention shows that Peptide-T has systematic C.N.S. effects similar to those drugs which are effective in patients with Dementia (neurotropics and/or cognitive activators).

Additionally, the data presented with this invention suggests that peptide T acts to reduce or eliminate the symptoms of TSP. Intranasal administration at 6 mg/day resulted in improvement in feet and legs paralysis, improvement in bladder and sexual function as well as improvement in memory and attention deficits. This suggests that the present invention acts to improve the neuromotor function of HTLV-1 infected patients.

What is claimed is:

1. A method of treating tropical spastic paresis in mammals which comprises administering an effective amount of a peptide of the formula (I):

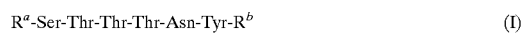

$$R^a\text{-Ser-Thr-Thr-Thr-Asn-Tyr-}R^b \quad \text{(I)}$$

where $R^a$ represents an amino terminal residue Ala-, D-Ala- or Cys-Ala- and $R^b$ represents a carboxy terminal residue -Thr, -Thr-amide, -Thr-Cys or Thr-Cys-amide; or a peptide of formula (II):

$$R^1\text{-}R^2\text{-}R^3\text{-}R^4\text{-}R^5 \quad \text{(II)}$$

where $R^1$ is an amino acid terminal residue $XR^6$ or $R^6$ wherein $R^6$ is Thr-, Ser-, Asn-, Leu-, Ile-, Arg-, or Glu- and X is Cys, $R^2$ is Thr, Ser, or Asp, $R^3$ is Thr, Ser, Asn, Arg, Gln, Lys or Trp, $R^4$ is Tyr, and $R^5$ is a carboxy terminal residue which is $R^7X$ or $R^7$ wherein $R^7$ is Thr, Arg or Gly and X is Cys or a physiologically acceptable salt thereof.

2. A method for treating tropical spastic paresis in mammals which comprises administering an effective amount of a peptide of the formula (I):

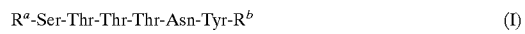

$$R^a\text{-Ser-Thr-Thr-Thr-Asn-Tyr-}R^b \quad \text{(I)}$$

where $R^a$ represents an amino terminal residue Ala-, D-Ala, or Cys-Ala- and $R^b$ represents a carboxy terminal residue -Thr, -Thr-amide, -Thr-Cys or -Thr-Cys amide, or a peptide of formula (II):

$$R^1\text{-}R^2\text{-}R^3\text{-}R^4\text{-}R^5 \quad \text{(II)}$$

where $R^1$ represents an amino terminal residue Thr-, Ser- or Asn-, $R^2$ is Thr, Ser or Asp, $R^3$ is Thr, Ser, Asn or Arg, $R^4$ is Tyr, and $R^5$ is a carboxy terminal residue -Thr, -Thr-amide, -Thr-Cys, -Thr-Cys-amide, -Arg,-Arg-amide, -Arg-Cys, -Arg-Cys-amide, -Gly, -Gly-amide, -Gly-Cys or -Gly-Cys-amide, or a derivative thereof which is an ester or an amide, or a physiologically acceptable salt thereof.

3. A method of treating tropical spastic paresis in mammals which comprises administering an effective blocking amount of a peptide of the formula (I):

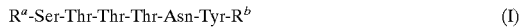

$R^a$-Ser-Thr-Thr-Thr-Asn-Tyr-$R^b$    (I)

where $R^a$ represents an amino terminal residue Ala-, D-Ala- or Cys-Ala- and $R^b$ represents a carboxy terminal residue -Thr, -Thr-amide, -Thr-Cys or Thr-Cys-amide; or a peptide of formula (III):

$R^1$-$R^2$-$R^3$-$R^4$    (III)

where
- $R^1$ is an amino acid terminal residue Thr-, Cys-Thr-, Ser-, Cys-Ser-, Asn-, Cys-Asn-, Glu-, Cys-Glu-, Arg-, Cys-Arg-, Ile-, Cys-Ile-, Leu-, or Cys-Leu-,
- $R^2$ is Thr, Ser, or Asp,
- $R^3$ is Thr, Ser, Asn, Arg, Gln, Lys or Trp, and
- $R^4$ is a carboxy terminal Tyr or -Tyr-Cys.

4. The method of claim 1 wherein the peptide used is a peptide of the formula (II) and wherein $R^1$ is $XR^6$ and $R^5$ is $R^7X$.

5. A method of claim 1 wherein the disease is caused by HTLV-1 virus.

6. A method according to any one of claims 1 to 4 wherein said peptide is administered intranasally.

7. A method for improving neuromotor function of HTLV-1 infected patients which comprises intranasally administering an effective amount of a peptide of formula (III):

$R^1$-$R^2$-$R^3$-$R^4$    (III)

where
- $R^1$ is an amino acid terminal residue Thr-, Cys-Thr-, Ser-, Cys-Ser-, Asn-, Cys-Asn-, Glu-, Cys-Glu-, Arg-, Cys-Arg-, Ile-, Cys-Ile-, Leu-, or Cys-Leu-,
- $R^2$ is Thr, Ser, or Asp,
- $R^3$ is Thr, Ser, Asn, Arg, Gln, Lys or Trp, and
- $R^4$ is a carboxy terminal -Tyr or -Tyr-Cys.

8. The method according to claim 1, wherein said peptide is administered intranasally, daily, in three substantially equally spaced applications, the combined applications containing a total of about 1.2 mg of said peptide.

9. The method according to claim 2, wherein said peptide is administered intranasally, daily, in three substantially equally spaced applications, the combined applications containing a total of about 1.2 mg of said peptide.

10. The method according to claim 3, wherein said peptide is administered intranasally, daily, in three substantially equally spaced applications, the combined applications containing a total of about 1.2 mg of said peptide.

11. The method according to claim 7, wherein said peptide is administered intranasally, daily, in three substantially equally spaced applications, the combined applications containing a total of about 1.2 mg of said peptide.

12. The method according to claim 1, wherein said peptide is administered intranasally, daily, in three substantially equally spaced applications, the combined applications containing a total of about 6.0 mg of said peptide.

13. The method according to claim 2, wherein said peptide is administered intranasally, daily, in three substantially equally spaced applications, the combined applications containing a total of about 6.0 mg of said peptide.

14. The method according to claim 3, wherein said peptide is administered intranasally, daily, in three substantially equally spaced applications, the combined applications containing a total of about 6.0 mg of said peptide.

15. The method according to claim 7, wherein said peptide is administered intranasally, daily, in three substantially equally spaced applications, the combined applications containing a total of about 6.0 mg of said peptide.

16. The method according to claim 1, wherein said peptide is administered intranasally, daily, in three substantially equally spaced applications, the combined applications containing a total of about 30.0 mg of said peptide.

17. The method according to claim 2, wherein said peptide is administered intranasally, daily, in three substantially equally spaced applications, the combined applications containing a total of about 30.0 mg of said peptide.

18. The method according to claim 3, wherein said peptide is administered intranasally, daily, in three substantially equally spaced applications, the combined applications containing a total of about 30.0 mg of said peptide.

19. The method according to claim 7, wherein said peptide is administered intranasally, daily, in three substantially equally spaced applications, the combined applications containing a total of about 30.0 mg of said peptide.

* * * * *